(12) United States Patent
Shalev

(10) Patent No.: US 6,853,858 B2
(45) Date of Patent: Feb. 8, 2005

(54) ADMINISTRATION OF ANTI-INFLAMMATORY DRUGS INTO THE CENTRAL NERVOUS SYSTEM

(75) Inventor: Alon Shalev, Ra'anana (IL)

(73) Assignee: Brainsgate, Ltd., Ra'anana (IL)

(*) Notice: Subject to any disclaimer, the term of this patent is extended or adjusted under 35 U.S.C. 154(b) by 190 days.

(21) Appl. No.: 10/294,343

(22) Filed: Nov. 14, 2002

(65) Prior Publication Data

US 2003/0176892 A1 Sep. 18, 2003

Related U.S. Application Data

(63) Continuation-in-part of application No. 10/258,714, filed on Jan. 22, 2003.
(60) Provisional application No. 60/203,172, filed on May 8, 2000, provisional application No. 60/388,931, filed on Jun. 14, 2002, provisional application No. 60/400,167, filed on Jul. 31, 2002, and provisional application No. 60/364,451, filed on Mar. 15, 2002.

(51) Int. Cl.$^7$ ............................................. A61N 1/40
(52) U.S. Cl. .............................. 607/3; 604/20; 604/514
(58) Field of Search .............................. 607/3, 45, 46; 604/20, 522, 514, 94.01; 128/200.14

(56) References Cited

U.S. PATENT DOCUMENTS

| | | | |
|---|---|---|---|
| 4,152,928 A | 5/1979 | Roberts | |
| 4,319,580 A | 3/1982 | Colley et al. | |
| 4,886,493 A | 12/1989 | Yee | |
| 5,031,618 A | 7/1991 | Mullett | |
| 5,693,077 A | * 12/1997 | Friedman | ...................... 607/96 |

(List continued on next page.)

FOREIGN PATENT DOCUMENTS

| | | |
|---|---|---|
| WO | WO 99/03473 | 1/1999 |
| WO | WO 00/44432 | 8/2000 |
| WO | WO 01/43733 | 6/2001 |

OTHER PUBLICATIONS

Branston NM, "The physiology of the cerebrovascular parasympathetic innervation," British Journal of Neurosurgery 9:319–329 (1995).

(List continued on next page.)

*Primary Examiner*—Mark Bockelman
(74) *Attorney, Agent, or Firm*—Abelman, Frayne & Schwab

(57) ABSTRACT

Apparatus is provided for delivering a Non Steroidal Anti-Inflammatory Drug (NSAID) supplied to a body of a subject for delivery to at least a portion of a central nervous system (CNS) of the subject via a systemic blood circulation of the subject, including a stimulator adapted to stimulate at least one site of the subject, so as to cause an increase in passage of the NSAID from the systemic blood circulation across a blood brain barrier (BBB) of the subject to the portion of the CNS, during at least a portion of the time that the NSAID is present in the blood, the site selected from the list consisting of: a sphenopalatine ganglion (SPG) of the subject, an anterior ethmoidal nerve of the subject, a posterior ethmoidal nerve of the subject, a communicating branch between an anterior ethmoidal nerve and a retro-orbital branch of an SPG of the subject, a communicating branch between a posterior ethmoidal nerve and a retro-orbital branch of an SPG of the subject, a greater palatine nerve of the subject, a lesser palatine nerve of the subject, a sphenopalatine nerve of the subject, a communicating branch between a maxillary nerve and an SPG of the subject, a nasopalatine nerve of the subject, a posterior nasal nerve of the subject, an infraorbital nerve of the subject, an otic ganglion of the subject, an afferent fiber going into the otic ganglion of the subject, an efferent fiber going out of the otic ganglion of the subject, a vidian nerve of the subject, a greater superficial petrosal nerve of the subject, and a lesser deep petrosal nerve of the subject.

44 Claims, 8 Drawing Sheets

U.S. PATENT DOCUMENTS

| | | | |
|---|---|---|---|
| 5,855,907 | A | 1/1999 | Peyman |
| 5,938,690 | A | 8/1999 | Law et al. |
| 6,405,079 | B1 | 6/2002 | Ansarinia |
| 6,432,986 | B2 | 8/2002 | Levin |
| 6,491,940 | B1 | 12/2002 | Levin |
| 6,526,318 | B1 | 2/2003 | Ansarinia |
| 6,647,980 | B1 * | 11/2003 | Gizurarson ............ 128/200.14 |
| 6,678,553 | B2 * | 1/2004 | Lerner et al. .................. 604/20 |
| 2001/0004644 | A1 | 6/2001 | Levin |
| 2003/0133877 | A1 | 7/2003 | Levin |

OTHER PUBLICATIONS

Branston NM et al., "Contribution of cerebrovascular parasympathetic and sensory innervation to the short–term control of blood flow in rat cerebral cortex," J Cereb Blood Flow Metab 15(3):525–31 (1995).

Toda N et al., "Cerebral vasodilation induced by stimulation of the pterygopalatine ganglion and greater petrosal nerve in anesthetized monkeys," Neuroscience 96(2):393–398 (2000).

Seylaz J et al., "Effect of stimulation of the sphenopalatine ganglion on cortical blood flow in the rat," J Cereb Blood Flow Metab 8(6):875–8 (1988).

Rucci L et al., "Histamine release from nasal mucosal mast cells in patients with chronic hypertrophic non–allergic rhinitis, after parasympathetic nerve stimulation," Agents Actions 25(3–4):314–20 (1988).

L. Rucci, et al, "Effects of Vidian Nerve Stimulation on the Nasal and Maxillary Sinus Mucosa", The Journal of Laryngology and Otology, Jun. 1984, vol. 98, pp. 597–607.

N. Toda, et al, "Preganglionic and Postganglionic Neurons Responsible for Cerebral Vasodilation Mediated by Nitric Oxide in Anesthetized Dogs", J Cereb Blood Flow Metab. vol. 20 No. 4, 2000.

Ronald F. Young, "Electrical Stimulation of the Trigeminal nerve root for the Treatment of Chronic Facial Pain", J Neurosurg 83:72–78, 1995.

L. Rucci, et al, "Vidian Nerve Resection in Chronic Hypertrophic Non Allergic Rhinitis: Effects on Histamine Content, Number and Rate of Degranulation Processes of Mast Cells in Nasal Mucosa", Rhinology, 23, 309–314, 1985.

L. Rucci, et al, "Tympanometric Variations Induced by Vidian Nerve Stimulation in Humans", The Journal of Laryngology and Otology, Apr. 1985, vol. 99, pp. 355–358.

E. Masini, et al, "Stimulation and Resection of Vidian Nerve in Patients with Chronic hypertrophic Non–Allergic Rhinitis: Effect on Histamine Content in Nasal Mucosa", Agents and Actions, vol. 18, ½ 1986.

H. Bolay, et al, "Intrinsic Brain Activity Triggers Trigeminal Meningeal Afferents in a Migraine Model", Feb. 2002, vol. 8 No. 2, pp. 136–142.

N. Suzuki, et al, "Origins and Pathways of Cerebrovascular Vasoactive Intestinal Polypeptide–Positive Nerves in Rat", J Cereb Blood Flow Metab. vol. 8 No. 5, 1988.

Delephine, et al., "Plasma Protein Extravasation Induced in the Rat Dura Mater by Stimulation of the Parasympathetic Sphenopalatine Ganglion", Experimental Neurology, 147, 389–400, 1997.

Hara H. Zhang, et al., "Parasympathetic Cerebrovascular Innervation: An Anterograde Tracing from the Sphenopalatine Ganglion in the Rat", Neurosurgery, 32, 822–827, 1993.

G.L. Ruskell, "The Orbital Branches of the Pterygopalatine Ganglion and their Relationship with Internal Carotid Nerve Branches in Primates", J. Anat. 1970, 106, 2, pp. 323–339.

Kroll RA, Neuwelt EA, "Outwitting the Blood Brain Barrier for Therapeutic Purposes: Osmotic Opening and Other Means", Neurosurgery, 42, 1083–1100, 1998.

Sanders M, et al., "Efficacy of Sphenopalatine Ganglion Blockade in 66 Patients Suffering from Cluster Headache: A 12–70 Month Follow–Up Evaluation", Journal of Neurosurgery, 87, 876–880, 1997.

Gloria Lee, et al, "Drug Transporters in the Central Nervous System: Brain Barriers and Brain Perenchyma Considerations", Pharmacol Rev vol. 53, No. 4, pp. 569–596, 2001.

Van de WaterBeemd, et al., "Estimation of Blood Brain Barrier Crossing of Drugs Using Molecular Size and Shape and H bonding Descriptors", Journal of Drug Targeting, 6, 151–165, 1998.

Suzuki, N. et al., "Selective Electrical Stimulation of postganglionic Cerebrovascular Parasympathetic Nerve Fibers Originating from the Sphenopalatine Ganglion Enhances Cortical Blood Flow in the Rat", Journal of Cerebral Blood Flow and Metabolism, 10, 383–391 (1990).

Suzuki, N. et al., "Effect on Cortical Blood Flow of Electrical Stimulation of Trigeminal Cerebrovascular Nerve Fibers in the Rat", Acta Physiol. Scand., 138, 307–315, 1990.

Samad TA et al., in an article entitled, "Interleukin–1beta–mediated induction of Cox–2 in the CNS contributes to inflammatory pain hypersensitivity," in Nature 410(6827):471–5 (2001).

Major A, Silver W, "Odorants presented to the rat nasal cavity increase cortical blood flow," Chem. Senses, 24, 665–669 (1999).

Fusco BM, Fiore G, Gallo F, Martilletti P, Giacovazzo M, "'Capsaicin–sensitive' sensory neurons in cluster headache: pathophysiological aspects and therapeutic indications," Headache, 34, 132–137 (1994).

Lambert GA, Bogduk N, Goadsby PJ, Duckworth JW, Lance JW, "Decreased carotid arterial resistance in cats in response to trigeminal stimulation," Journal of Neurosurgery, 61, 307–315 (1984).

Silver WL, "Neural and pharmacological basis for nasal irritation," in Tucker WG, Leaderer BP, Molhave L, Cain WS (eds), Sources of Indoor Air Contaminants, Ann. NY Acad. Sci., 641, 152–163 (1992).

* cited by examiner

US 6,853,858 B2

ADMINISTRATION OF ANTI-INFLAMMATORY DRUGS INTO THE CENTRAL NERVOUS SYSTEM

CROSS-REFERENCE TO RELATED APPLICATIONS

This application is a continuation-in-part of a U.S. patent application Ser. No. 10/258,714 Shalev and Gross, filed Jan. 22, 2003 entitled, "Method and apparatus for stimulating the sphenopalatine ganglion to modify properties of the EBB and cerebral blood flow," which is a U.S. national phase application corresponding to PCT Patent Application PCT/IL01/00402, filed May 7, 2001, entitled, "Method and apparatus for stimulating the sphenopalatine ganglion to modify properties of, the BBB and cerebral blood flow," which claims priority from U.S. Provisional Patent Application No. 60/203,172, filed May 8, 2000, entitled, "Method and apparatus for stimulating the sphenopalatine ganglion to modify properties of the EBB and cerebral blood flow."

This application claims priority from (i) U.S. Provisional Patent Application No. 60/364,451, filed Mar. 15, 2002 and filed Jun. 14, 2002, entitled, "Methods and systems for management of Alzheimer's disease," and (ii) U.S. Provisional Patent Application No. 60/400,167, filed Jul. 31, 2002, entitled, "Delivering compounds to the brain by modifying properties of the BBB and cerebral circulation."

This application is related to: (i) a U.S. provisional patent application to Lorian et al., filed on even date herewith, entitled, "Surgical tools and techniques for stimulation," (ii) a U.S. provisional patent application to Gross et al., filed on even date herewith, entitled, "Stimulation circuitry and control of electronic medical device," (iii) a U.S. patent application to Shalev et al., filed on even date herewith, entitled, "Stimulation for treating eye pathologies," and (iv) a U.S. provisional patent application to Shalev et al., filed on even date herewith, entitled, "Stimulation for treating ear pathologies."

Each of the above-cited patent applications is assigned to the assignee of the present patent application and is incorporated herein by reference.

FIELD OF THE INVENTION

The present invention relates generally to medical procedures and electrical devices. More specifically, the invention relates to the use of electrical, chemical, mechanical and/or odorant stimulation for administering anti-inflammatory drugs.

BACKGROUND OF THE INVENTION

The blood-brain barrier (BBB) is a unique feature of the central nervous system (CNS) which isolates the brain from the systemic blood circulation. To maintain the homeostasis of the CNS, the BBB prevents access to the brain of many substances circulating in the blood.

The BBB is formed by a complex cellular system of endothelial cells, astroglia, pericytes, perivascular macrophages, and a basal lamina. Compared to other tissues, brain endothelia have the most intimate cell-to-cell connections; endothelial cells adhere strongly to each other, forming structures specific to the CNS called "tight junctions" or zonula occludens. They involve two opposing plasma membranes which form a membrane fusion with cytoplasmic densities on either side. These tight junctions prevent cell migration or cell movement between endothelial cells. A continuous uniform basement membrane surrounds the brain capillaries. This basal lamina encloses contractile cells called pericytes, which form an intermittent layer and probably play some role in phagocytosis activity and defense if the BBB is breached. Astrocytic end feet, which cover the brain capillaries, build a continuous sleeve and maintain the integrity of the BBB by the synthesis and secretion of soluble growth factors (e.g., gamma-glutamyl transpeptidase) essential for the endothelial cells to develop their BBB characteristics.

Because of the BBB, certain non-surgical treatments of the brain based upon systemic introduction of compounds through the bloodstream have been ineffective or less effective. For example, chemotherapy has been relatively ineffective in the treatment of CNS metastases of systemic cancers (e.g., breast cancer, small cell lung cancer, lymphoma, and germ cell tumors), despite clinical regression and even complete remission of these tumors in non-CNS systemic locations. Important factors determining drug delivery from blood into the CNS are lipid solubility, molecular mass, and electrical charge. A good correlation exists between the lipid solubility of a drug, expressed as the octanol/water partition coefficient, and the drug's ability to penetrate or diffuse across the BBB. This is particularly relevant for drugs with molecular weights smaller than 600 dalton (Da). The normal BBB prevents the passage of ionized water soluble drugs with a molecular weight greater than 180 Da. Many currently-available effective chemotherapeutic agents, however, have a molecular weight between 200 and 1200 Da. Therefore, based both on their lipid solubilities, molecular masses, and/or other factors, the passage of many agents is impeded by the BBB.

In addition to transcellular diffusion of lipophilic agents, there are several specific transport mechanisms to carry certain molecules across the brain's endothelial cells. Specific transport proteins exist for required molecules, such as glucose and amino acids. Additionally, absorptive endocytosis and transcytosis occur for cationized plasma proteins. Specific receptors for certain proteins, such as transferrin and insulin, mediate endocytosis and transport across the cell.

Non-surgical treatment of neurological disorders is generally limited to systemic introduction of compounds such as neuropharmaceuticals and other neurologically-active agents that might remedy or modify neurologically-related activities and disorders. Such treatment is limited, however, by the relatively small number of known compounds that pass through the BBB. Even those that do cross the BBB often produce adverse reactions in other parts of the body.

There have been a number of different studies regarding efforts to cross the BBB—specifically, with regard to overcoming the limited access of drugs to the brain. Such efforts have included, for example, chemical modification, development of more hydrophobic analogs, or linking an active compound to a specific carrier. Transient opening of the BBB in humans has been achieved by intracarotid infusion of hypertonic mannitol solutions or bradykinin analogs. Also, modulation of the P-glycoprotein, whose substrates are actively pumped out of brain cells into capillary lumens, has been found to facilitate the delivery of drugs to the brain.

Many pathological conditions, such as stroke, migraine, and Alzheimer's disease, are significantly affected or exacerbated by abnormal cerebral blood flow.

PCT Patent Publication WO 01/85094 to Shalev and Gross, which is assigned to the assignee of the present patent application and is incorporated herein by reference, describes apparatus for modifying a property of a brain of a patient, including electrodes applied to a sphenopalatine ganglion (SPG) or a neural tract originating in or leading to the SPG. A control unit drives the electrodes to apply a current capable of inducing (a) an increase in permeability of a blood-brain barrier (BBB) of the patient, (b) a change in cerebral blood flow of the patient, and/or (c) an inhibition of parasympathetic activity of the SPG.

U.S. Pat. No. 5,756,071 to Mattern et al., which is incorporated herein by reference, describes a method for nasally administering aerosols of therapeutic agents to enhance penetration of the blood brain barrier. The patent describes a metering spray designed for pernasal application, the spray containing at least one sex hormone or at least one metabolic precursor of a sex hormone or at least one derivative of a sex hormone or combinations of these, excepting the precursors of testosterone, or at least one biogenic amine, with the exception of catecholamines.

U.S. Pat. No. 5,752,515 to Jolesz et al., which is incorporated herein by reference, describes apparatus for image-guided ultrasound delivery of compounds through the blood-brain barrier. Ultrasound is applied to a site in the brain to effect in the tissues and/or fluids at that location a change detectable by imaging. At least a portion of the brain in the vicinity of the selected location is imaged, e.g., via magnetic resonance imaging, to confirm the location of that change. A compound, e.g., a neuropharmaceutical, in the patient's bloodstream is delivered to the confirmed location by applying ultrasound to effect opening of the blood-brain barrier at that location and, thereby, to induce uptake of the compound there.

PCT Publication WO 01/97905 to Ansarinia, which is incorporated herein by reference, describes a method for the suppression or prevention of various medical conditions, including pain, movement disorders, autonomic disorders, and neuropsychiatric disorders. The method includes positioning an electrode on or proximate to at least one of the patient's SPG, sphenopalatine nerves, or vidian nerves, and activating the electrode to apply an electrical signal to such nerve. In a further embodiment for treating the same conditions, the electrode used is activated to dispense a medication solution or analgesic to such nerve. The '905 publication also describes surgical techniques for implanting the electrode.

U.S. Pat. No. 6,405,079 to Ansarinia, which is incorporated herein by reference, describes a method for the suppression or prevention of various medical conditions, including pain, movement disorders, autonomic disorders, and neuropsychiatric disorders. The method includes positioning an electrode adjacent to or around a sinus, the dura adjacent a sinus, or falx cerebri, and activating the electrode to apply an electrical signal to the site. In a further embodiment for treating the same conditions, the electrode dispenses a medication solution or analgesic to the site. The '079 patent also describes surgical techniques for implanting the electrode.

Samad T A et al., in an article entitled, "Interleukin-1beta-mediated induction of Cox-2 in the CNS contributes to inflammatory pain hypersensitivity," in Nature 410 (6827): 471–5 (2001), describe mechanisms that indicate that preventing central prostanoid production, by inhibiting the interleukin-1beta-mediated induction of Cox-2 in neurons or by inhibiting central Cox-2 activity, may reduce centrally-generated inflammatory pain hypersensitivity.

The following references, which are incorporated herein by reference, may be useful:

Delepine L, Aubineau P, "Plasma protein extravasation induced in the rat dura mater by stimulation of the parasympathetic sphenopalatine ganglion," Experimental Neurology, 147, 389–400 (1997)

Hara H, Zhang Q J, Kuroyanagi T, Kobayashi S, "Parasympathetic cerebrovascular innervation: An anterograde tracing from the sphenopalatine ganglion in the rat," Neurosurgery, 32, 822–827 (1993)

Jolliet-Riant P, Tillement J P, "Drug transfer across the blood-brain barrier and improvement of brain delivery," Fundam. Clin. Pharmacol., 13, 16–25 (1999)

Kroll R A, Neuwelt E A, "Outwitting the blood brain barrier for therapeutic purposes: Osmotic opening and other means," Neurosurgery, 42, 1083–1100 (1998)

Sanders M, Zuurmond W W, "Efficacy of sphenopalatine ganglion blockade in 66 patients suffering from cluster headache: A 12–70 month follow-up evaluation," Journal of Neurosurgery, 87, 876–880 (1997)

Syelaz J, Hara H. Pinard E, Mraovitch S, MacKenzie E T, Edvinsson L, "Effects of stimulation of the sphenopalatine ganglion on cortical blood flow in the rat," Journal of Cerebral Blood Flow and Metabolism," 8, 875–878 (1988)

Van de Waterbeemd H, Camenisch G, Folkers G, Chretien J R, Raevsky O A, "Estimation of blood brain barrier crossing of drugs using molecular size and shape and h bonding descriptors," Journal of Drug Targeting," 6, 151–165, (1998)

Suzuki N, Hardebo J E, Kahrstrom J, Owman C, "Selective electrical stimulation of postganglionic cerebrovascular parasympathetic nerve fibers originating from the sphenopalatine ganglion enhances cortical blood flow in the rat," Journal of Cerebral Blood Flow and Metabolism, 10, 383–391 (1990)

Suzuki N, Hardebo J E, Kahrstrom J, Owman C H, "Effect on cortical blood flow of electrical stimulation of trigeminal cerebrovascular nerve fibres in the rat," Acta Physiol. Scand., 138, 307–315 (1990)

Major A, Silver W, "Odorants presented to the rat nasal cavity increase cortical blood flow," Chem. Senses, 24, 665–669 (1999)

Fusco B M, Fiore G, Gallo F, Martelletti P, Giacovazzo M, "'Capsaicin-sensitive' sensory neurons in cluster headache: pathophysiological aspects and therapeutic indications," Headache, 34, 132–137 (1994)

Lambert G A, Bogduk N, Goadsby P J, Duckworth J W, Lance J W, "Decreased carotid arterial resistance in cats in response to trigeminal stimulation," Journal of Neurosurgery, 61, 307–315 (1984)

Silver W L, "Neural and pharmacological basis for nasal irritation," in Tucker W G, Leaderer B P, Molhave L, Cain W S (eds), Sources of Indoor Air Contaminants, Ann. NY Acad. Sci., 641, 152–163 (1992)

Silver W, "Chemesthesis: the burning questions," ChemoSense, Vol 2, 1–2 (1999)

Devoghel J C, "Cluster headache and sphenopalatine block," Acta Anaesthesiol Belg., 32 (1):101–7 (1981)

SUMMARY OF THE INVENTION

It is an object of some aspects of the present invention to provide improved methods and apparatus for delivery of compounds to the brain, particularly through the BBB.

It is also an object of some aspects of the present invention to provide such methods and apparatus as can be employed to deliver such compounds through the BBB with a minimally invasive approach.

It is a further object of some aspects of the present invention to provide such methods and apparatus as can facilitate delivery of large molecular weight compounds through the BBB.

It is yet a further object of some aspects of the present invention to provide cost-effective methods and apparatus for delivery of compounds through the blood-brain-barrier.

It is still a further object of some aspects of the present invention to provide improved methods and apparatus for remedying or modifying neurological activities and disorders via delivery of compounds through the blood-brain-barrier.

It is also a further object of some aspects of the present invention to provide improved methods and apparatus for delivery of Non Steroidal Anti-Inflammatory Drugs (NSAIDs) to the central nervous system, particularly through the BBB.

It is an additional object of some aspects of the present invention to provide improved methods and apparatus for modulating cerebral blood flow.

It is yet an additional object of some aspects of the present invention to provide improved methods and apparatus for treating migraine, cluster and other types of headaches.

It is still an additional object of some aspects of the present invention to provide improved methods and apparatus for treating neurological diseases (for example, Alzheimer's disease).

It is also an object of some aspects of the present invention to provide implantable apparatus which affects a property of the brain, without actually being implanted in the brain.

It is a further object of some aspects of the present invention to provide methods which affect a property of the brain without the use of implantable apparatus.

It is yet a further object of some aspects of the present invention to affect a property of the brain by using the neuroexcitatory and/or neuroinhibitory effects of odorants on nerves in the head.

These and other objects of the invention will become more apparent from the description of preferred embodiments thereof provided hereinbelow.

In some preferred embodiments of the present invention, the transport of Non Steroidal Anti-Inflammatory Drugs (NSAIDs) across the BBB into the brain, the spinal cord, or the eye is facilitated by stimulating at least one "modulation target site" (MTS), as defined hereinbelow, by applying electrical, chemical, mechanical and/or odorant stimulation to the site. Typically, the stimulation is applied in order to induce changes in cerebral blood flow and/or to modulate permeability of the blood-brain barrier (BBB).

In the present patent application, including the claims, a "modulation target site" (MTS) consists of:

a sphenopalatine ganglion (SPG) (also called a pterygopalatine ganglion);

an anterior ethmoidal nerve;

a posterior ethmoidal nerve;

a communicating branch between the anterior ethmoidal nerve and the SPG (retro orbital branch);

a communicating branch between the posterior ethmoidal nerve and the SPG (retro orbital branch);

a nerve of the pterygoid canal (also called a vidian nerve), such as a greater superficial petrosal nerve (a preganglionic parasympathetic nerve) or a lesser deep petrosal nerve (a postganglionic sympathetic nerve);

a greater palatine nerve;

a lesser palatine nerve;

a sphenopalatine nerve;

a communicating branch between the maxillary nerve and the sphenopalatine ganglion;

a nasopalatine nerve;

a posterior nasal nerve;

an infraorbital nerve;

an otic ganglion;

an afferent fiber going into the otic ganglion; or an efferent fiber going out of the otic ganglion.

It is to be appreciated that references herein to specific modulation target sites are to be understood as including other modulation target sites, as appropriate.

It is further to be appreciated that implantation and modulation sites, methods of implantation, and parameters of modulation are described herein by way of illustration and not limitation, and that the scope of the present invention includes other possibilities which would be obvious to someone of ordinary skill in the art who has read the present patent application.

It is yet further to be appreciated that while preferred embodiments of the invention are generally described herein with respect to electrical transmission of power and electrical modulation of tissue, other modes of energy transport may be used as well. Such energy includes, but is not limited to, direct or induced electromagnetic energy, radiofrequency (RF) transmission, mechanical vibration, ultrasonic transmission, optical power, and low power laser energy (via, for example, a fiber optic cable).

It is additionally to be appreciated that whereas preferred embodiments of the present invention are described with respect to application of electrical currents to tissue, this is to be understood in the context of the present patent application and in the claims as being substantially equivalent to applying an electrical field, e.g., by creating a voltage drop between two electrodes.

In some preferred embodiments of the present invention, stimulation of at least one MTS is achieved by presenting odorants to an air passage of a patient, such as a nasal cavity or the throat. The temporal profile and other quantitative characteristics of such odorant modulation are believed by the present inventors to have a mechanism of action that has a neuroanatomical basis overlapping with that of the electrical modulation of the SPG. Furthermore, experimental animal evidence collected by the inventors and described in a U.S. provisional patent application to Shalev and Gross entitled, "SPG stimulation," filed Mar. 28, 2002, which is assigned to the assignee of the present invention and is incorporated herein by reference, suggest a correlation between the mechanisms of increasing cerebral blood flow and increased cerebrovascular permeability. For some applications, odorant-presentation techniques for treating an eye condition described herein are practiced in combination with techniques described in U.S. Provisional Patent Application No. 60/376,048, filed Apr. 25, 2002, entitled, "Methods and apparatus for modifying properties of the BBB and cerebral circulation by using the neuroexcitatory and/or neuroinhibitory effects of odorants on nerves in the head," which is assigned to the assignee of the present patent application and is incorporated herein by reference.

Odorants that may increase or decrease cerebral blood flow and/or the permeability of the BBB include, but are not limited to, propionic acid, cyclohexanone, amyl acetate, acetic acid, citric acid, carbon dioxide, sodium chloride, ammonia, menthol, alcohol, nicotine, piperine, gingerol, gingerone, allyl isothiocyanate, cinnamaldehyde, cuminaldehyde, 2-propenyl/2-phenylethyl isothiocyanate, thymol, and eucalyptol.

The odorants reach the appropriate neural structures and induce vasodilatation, vasoconstriction and/or cerebrovascular permeability changes. Delivery of a drug can be achieved by mixing the drug with the odorant; by intravenously, intraperitoneally, or intramuscularly administering the drug while the odorant is having an effect, or therebefore; or by other delivery methods known in the art.

In some preferred embodiments of the present invention, stimulation of at least one MTS is achieved by applying a neuroexcitatory agent to the MTS. Suitable neuroexcitatory agents include, but are not limited to acetylcholine and urocholine. For some applications, the MTS is stimulated by applying a neuroinhibitory agent, such as atropine, hexamethonium, or a local anesthetic (e.g., lidocaine).

In some preferred embodiments of the present invention, stimulation of the MTS is achieved by applying mechanical stimulation to the MTS, e.g., vibration.

As described above, it is believed that substantially all pharmacological treatments aimed at cerebral cells (for example those used for treating neurological and psychiatric disorders and pathologies) are amenable for use in combination with techniques described herein, including electrical, odorant, chemical and mechanical techniques for stimulating at least one MTS. In particular, these embodiments of the present invention may be adapted for use in facilitating the administration of Non Steroidal Anti-Inflammatory Drugs (NSAIDs) to the CNS, including the brain and the spinal cord, or to the eye or ear. These techniques facilitate the delivery of NSAIDs to the CNS to treat (a) conditions of the CNS, including neurodegenerative and inflammatory conditions, and (b) peripheral conditions, including inflammatory conditions. Examples of conditions of the CNS that typically benefit from these techniques include inflammation of the brain; headaches, including migraines; neurodegenerative diseases; Alzheimer's disease; depression; lethargy; loss of appetite; multiple sclerosis; psychic disturbances (e.g., AIDS-related psychic disturbances); dementia (of known or unknown cause); and viral and bacterial infections. Examples of peripheral conditions that typically benefit from these techniques include muscle and joint pain, often caused by inflammation and/or infection. For some applications, these techniques are effective in treating peripheral conditions by means of mechanisms described in the above-cited article to Samad T A et al., or by means of other mechanisms.

Advantageously, for some applications, use of the techniques described herein generally allows substantially more NSAID molecules to cross the BBB than would otherwise be possible. Although NSAID molecules are typically relatively small (about 250 Da), they generally exhibit about 99.9% plasma binding, which substantially inhibits their passage across the BBB. Use of the techniques described herein generally allows more NSAID molecules that are bound to high molecular weight compounds (e.g., albumin) to cross the BBB than would otherwise be possible.

Further advantageously, for some applications, the use of the techniques described herein for increasing the permeability of the BBB generally allows the administration of a lower dosage of an NSAID in order to deliver a given dosage of the NSAID to the CNS, than would otherwise be necessary. Administration of such a lower dosage typically reduces any unwanted side-effects that may be associated with the use of NSAIDs.

There is therefore provided, in accordance with an embodiment of the present invention, apparatus for delivering a Non Steroidal Anti-Inflammatory Drug (NSAID) supplied to a body of a subject for delivery to at least a portion of a central nervous system (CNS) of the subject via a systemic blood circulation of the subject, including a stimulator adapted to stimulate at least one site of the subject, so as to cause an increase in passage of the NSAID from the systemic blood circulation across a blood brain barrier (BBB) of the subject to the portion of the CNS, during at least a portion of the time that the NSAID is present in the blood, the site selected from the list consisting of: a sphenopalatine ganglion (SPG) of the subject, an anterior ethmoidal nerve of the subject, a posterior ethmoidal nerve of the subject, a communicating branch between an anterior ethmoidal nerve and a retro-orbital branch of an SPG of the subject, a communicating branch between a posterior ethmoidal nerve and a retro-orbital branch of an SPG of the subject, a greater palatine nerve of the subject, a lesser palatine nerve of the subject, a sphenopalatine nerve of the subject, a communicating branch between a maxillary nerve and an SPG of the subject, a nasopalatine nerve of the subject, a posterior nasal nerve of the subject, an infraorbital nerve of the subject, an otic ganglion of the subject, an afferent fiber going into the otic ganglion of the subject, an efferent fiber going out of the otic ganglion of the subject, a vidian nerve of the subject, a greater superficial petrosal nerve of the subject, and a lesser deep petrosal nerve of the subject.

In an embodiment, the stimulator is adapted to configure the stimulation to treat a condition of the CNS of the subject. The condition may include one or more of the following:

depression of the subject;

lethargy of the subject;

a loss of appetite of the subject;

multiple sclerosis of the subject;

a psychic disturbance of the subject;

dementia of the subject;

a neurodegenerative condition;

an infection of the subject;

inflammation of a brain of the subject;

a headache of the subject; or a migraine headache of the subject.

In an embodiment, the stimulator is adapted to configure the stimulation to treat a peripheral condition of the subject. The condition may include one or more of the following:

pain in a joint of the subject;

pain in a muscle of the subject;

pain caused by an infection of the subject; or pain caused by an inflammation of the subject.

In an embodiment, the stimulator includes an electrical stimulator, adapted to drive a current into the site, so as to stimulate the site. In an embodiment, the electrical stimulator is adapted to be implanted in a body of the subject.

In an embodiment, the electrical stimulator includes:

at least one electrode, adapted to be placed in a vicinity of the site; and a control unit, adapted to drive the electrode to apply the current to the site.

In an embodiment, the electrode is adapted to be implanted in the vicinity of the site.

In an embodiment, the site includes a first site and a second site, different from the first site, and the at least one electrode includes a first electrode and a second electrode, the first electrode adapted to be placed in a vicinity of the first site, and the second electrode adapted to be placed in a vicinity of the second site. In an embodiment, the first site includes the vidian nerve of the subject, and the second site includes the SPG of the subject, and the first electrode is adapted to be placed in a vicinity of the vidian nerve, and the second electrode is adapted to be placed in a vicinity of the SPG.

In an embodiment, the stimulator includes a chemical stimulator device, adapted to apply a chemical to the site, so as to stimulate the site. In an embodiment, the chemical includes a neuroexcitatory agent, and the chemical stimulator device is adapted to apply the neuroexcitatory agent. In an embodiment, the neuroexcitatory agent includes acetylcholine, and the chemical stimulator device is adapted to apply the acetylcholine.

In an embodiment, the stimulator includes a mechanical stimulator device, adapted to apply mechanical stimulation to the site. In an embodiment, the mechanical stimulator device is adapted to apply vibration to the site.

There is also provided, in accordance with an embodiment of the present invention, a method for delivering a Non Steroidal Anti-Inflammatory Drug (NSAID) to at least a portion of a central nervous system (CNS) of a subject, including:

supplying the NSAID to a systemic blood circulation of the subject;

stimulating at least one site of the subject, the site selected from the list consisting of: a sphenopalatine ganglion of the subject, an anterior ethmoidal nerve of the subject, a posterior ethmoidal nerve of the subject, a communicating branch between an anterior ethmoidal nerve and a retro-orbital branch of an SPG of the subject, a communicating branch between a posterior ethmoidal nerve and a retro-orbital branch of an SPG of the subject, a greater palatine nerve of the subject, a lesser palatine nerve of the subject, a sphenopalatine nerve of the subject, a communicating branch between a maxillary nerve and an SPG of the subject, a nasopalatine nerve of the subject, a posterior nasal nerve of the subject, an infraorbital nerve of the subject, an otic ganglion of the subject, an afferent fiber going into the otic ganglion of the subject, an efferent fiber going out of the otic ganglion of the subject, a vidian nerve of the subject, a greater superficial petrosal nerve of the subject, and a lesser deep petrosal nerve of the subject; and configuring the stimulation so as to cause an increase in passage of the NSAID from the systemic blood circulation across a blood brain barrier (BBB) of the subject to the portion of the CNS, during at least a portion of the time that the NSAID is present in the blood.

The present invention will be more fully understood from the following detailed description of the preferred embodiments thereof, taken together with the drawings, in which:

DETAILED DESCRIPTION OF THE INVENTION

Figure 1:
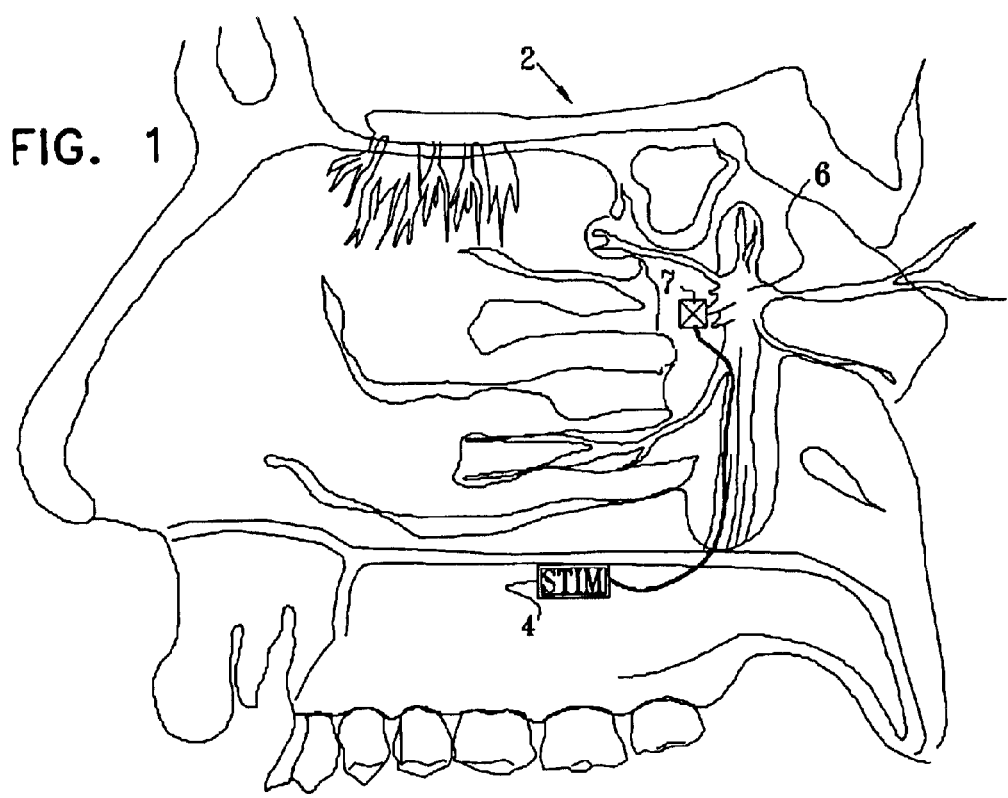
FIG. 1 is a schematic pictorial view of a fully implantable stimulator for stimulation of an MTS, in accordance with a preferred embodiments of the present invention.

FIG. 1 is a schematic pictorial view of a fully-implantable stimulator 4, for stimulation of a "modulation target site" (MTS), as defined hereinbelow, such as a sphenopalatine ganglion (SPG) 6, in accordance with a preferred embodiments of the present invention. In FIG. 1, a human nasal cavity 2 is shown, and stimulator 4 is implanted between the hard palate and the mucoperiosteum (not shown) of the roof of the mouth. Branches of parasympathetic neurons coming from SPG 6 extend to the middle cerebral and anterior cerebral arteries (not shown). Preferably, one or more relatively short electrodes 7 extend from stimulator 4 to contact or to be in a vicinity of an MTS, such as SPG 6.

In the present patent application and the claims, a "modulation target site" consists of:

a sphenopalatine ganglion (SPG) (also called a pterygopalatine ganglion);

an anterior ethmoidal nerve;

a posterior ethmoidal nerve;

a communicating branch between the anterior ethmoidal nerve and the SPG (retro orbital branch);

a communicating branch between the posterior ethmoidal nerve and the SPG (retro orbital branch);

a nerve of the pterygoid canal (also called a vidian nerve), such as a greater superficial petrosal nerve (a preganglionic parasympathetic nerve) or a lesser deep petrosal nerve (a postganglionic sympathetic nerve);

a greater palatine nerve;

a lesser palatine nerve;

a sphenopalatine nerve;

a communicating branch between the maxillary nerve and the sphenopalatine ganglion;

a nasopalatine nerve;

a posterior nasal nerve;

an infraorbital nerve;

an otic ganglion;

an afferent fiber going into the otic ganglion; or an efferent fiber going out of the otic ganglion.

For some applications, stimulator 4 is implanted on top of the bony palate, in the bottom of the nasal cavity. Alternatively or additionally, the stimulator is implanted at the lower side of the bony palate, at the top of the oral cavity. In this instance, one or more flexible electrodes 7 originating in the stimulator are passed through the palatine bone or posterior to the soft palate, so as to be in a position to stimulate the SPG or another MTS. Further alternatively or additionally, the stimulator may be directly attached to the SPG and/or to another MTS.

For some applications, stimulator 4 is delivered to a desired point within nasal cavity 2 by removably attaching stimulator 4 to the distal end of a rigid or slightly flexible introducer rod (not shown) and inserting the rod into one of the patient's nasal passages until the stimulator is properly positioned. As appropriate, the placement process may be facilitated by fluoroscopy, x-ray guidance, fine endoscopic surgery (FES) techniques or by any other effective guidance method known in the art, or by combinations of the aforementioned. Preferably, the ambient temperature and/or cerebral blood flow is measured concurrently with insertion. The cerebral blood flow may be measured with, for example, a laser Doppler unit positioned at the patient's forehead or transcranial Doppler measurements. Verification of proper implantation of the electrodes onto the appropriate neural structure may be performed by activating the device, and generally simultaneously monitoring cerebral blood flow.

The passage of certain molecules from cerebral blood vessels into the brain is hindered by the BBB. The endothelium of the capillaries, the plasma membrane of the blood vessels, and the foot processes of the astrocytes all impede uptake by the brain of the molecules. The BBB generally allows only small molecules (e.g., hydrophilic molecules of molecular weight less than about 200 Da, and lipophilic molecules of less than about 500 Da) to pass from the circulation into the brain.

In accordance with a preferred embodiment of the present invention, parasympathetic activation induced by current from stimulator 4 overcomes the resistance to trans-BBB molecular movement generated by the endothelium of the cerebral capillaries and the plasma membrane. For some applications, therefore, stimulator 4 may be used to transiently remove a substantial obstacle to the passage of drugs from the blood to the brain. For example, the stimulator may cyclically apply current for about two minutes, and subsequently have a rest period of between about 1 and 20 minutes.

It is hypothesized that two neurotransmitters play an important role in this change in properties of the BBB—vasoactive intestinal polypeptide (VIP) and nitric oxide (NO). (Acetylcholine may also be involved.) VIP is a short peptide, and NO is a gaseous molecule. VIP is believed to be a major factor in facilitating plasma protein extravasation (PPE), while NO is responsible for vasodilation. For some applications, stimulator 4 is adapted to vary parameters of the current applied to an MTS, as appropriate, in order to selectively influence the activity of one or both of these neurotransmitters. For example, stimulation of the parasympathetic nerve at different frequencies can induce differential secretion—low frequencies cause secretion of NO, while high frequencies (e.g., above about 10 Hz) cause secretion of peptides (VIP).

For other applications, a constant level DC signal, or a slowly varying voltage ramp is applied, in order to block parasympathetic neural activity in affected tissue. Alternatively, similar results can be obtained by stimulating at a rate higher than about 10 Hz, because this tends to exhaust neurotransmitters. Thus, stimulator 4 may be configured to induce parasympathetic electrical block, in order to cause vasoconstriction by mimicking the overall effect of chemical block on the SPG. This vasoconstrictive effect may be used, for example, to controllably prevent or reverse the formation of migraine headaches.

Figure 2:
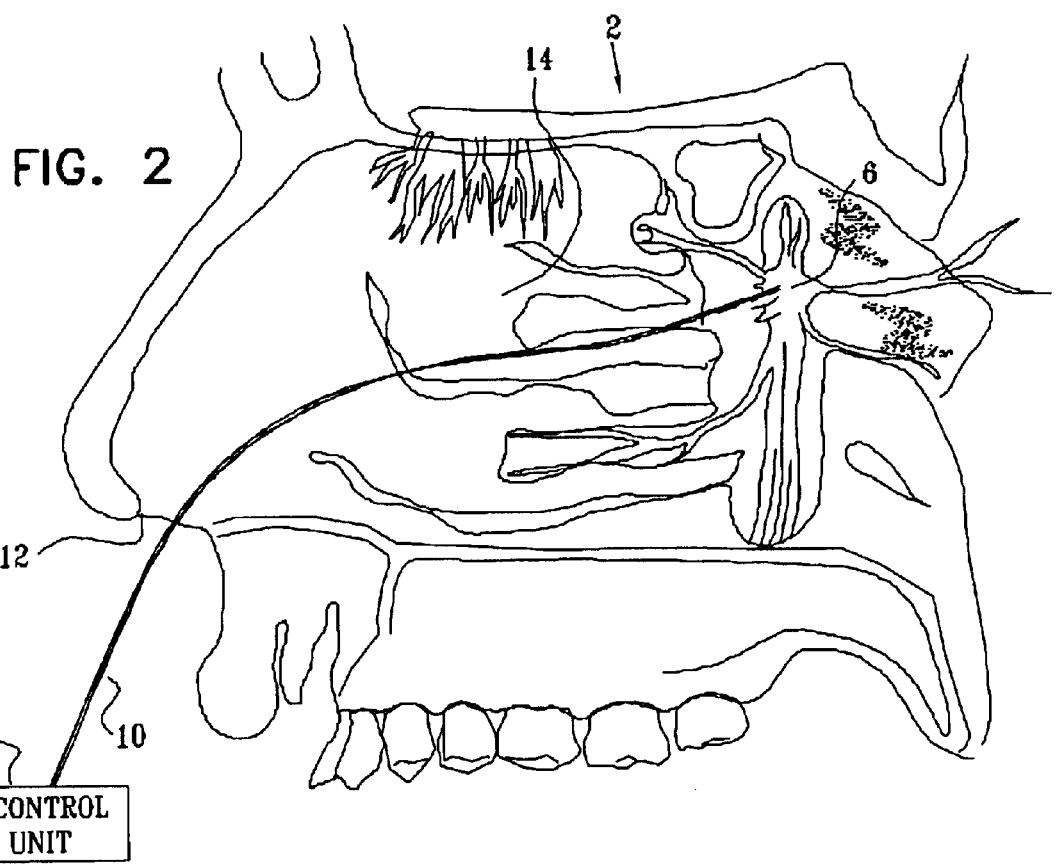
FIG. 2 is a schematic pictorial view of another stimulator for stimulation of an MTS, in accordance with a preferred embodiment of the present invention.

FIG. 2 is a schematic illustration of a stimulator control unit 8 positioned external to a patient's body, in accordance with a preferred embodiment of the present invention. At least one flexible electrode 10 preferably extends from control unit 8, through a nostril 12 of the patient, and to a position within the nasal cavity 14 that is adjacent to SPG 6.

It is to be understood that electrodes 7 (FIG. 1) and 10 may each comprise one or more electrodes, e.g., two electrodes, or an array of microelectrodes. For applications in which stimulator 4 comprises a metal housing that can function as an electrode, then typically one electrode 7 is used, operating in a monopolar mode. Regardless of the total number of electrodes in use, typically only a single or a double electrode extends to SPG 6. Other electrodes 7 or 10 or a metal housing of stimulator 4 are preferably temporarily or permanently implanted in contact with other parts of nasal cavity 2.

Each of electrodes 7 and/or 10 preferably comprises a suitable conductive material, for example, a physiologically-acceptable material such as silver, iridium, platinum, a platinum iridium alloy, titanium, nitinol, or a nickel-chrome alloy. For some applications, one or more of the electrodes have lengths ranging from about 1 to 5 mm, and diameters ranging from about 50 to 100 microns. Each electrode is preferably insulated with a physiologically-acceptable material such as polyethylene, polyurethane, or a co-polymer of either of these. The electrodes are preferably spiral in shape, for better contact, and may have a hook shaped distal end for hooking into or near the SPG. Alternatively or additionally, the electrodes may comprise simple wire electrodes, spring-loaded "crocodile" electrodes, or adhesive probes, as appropriate.

In a preferred embodiment of the invention, each one of electrodes 7 and/or 10 comprises a substantially smooth surface, except that the distal end of each such electrode is configured or treated to have a large surface area. For example, the distal tip may be porous platinized. Alternatively or additionally, at least the tip of electrode 7 or 10, and/or a metal housing of stimulator 4 includes a coating comprising an anti-inflammatory drug, such as beclomethasone sodium phosphate or beclomethasone phosphate. Alternatively, such an anti-inflammatory drug is injected or otherwise applied.

Figure 3:
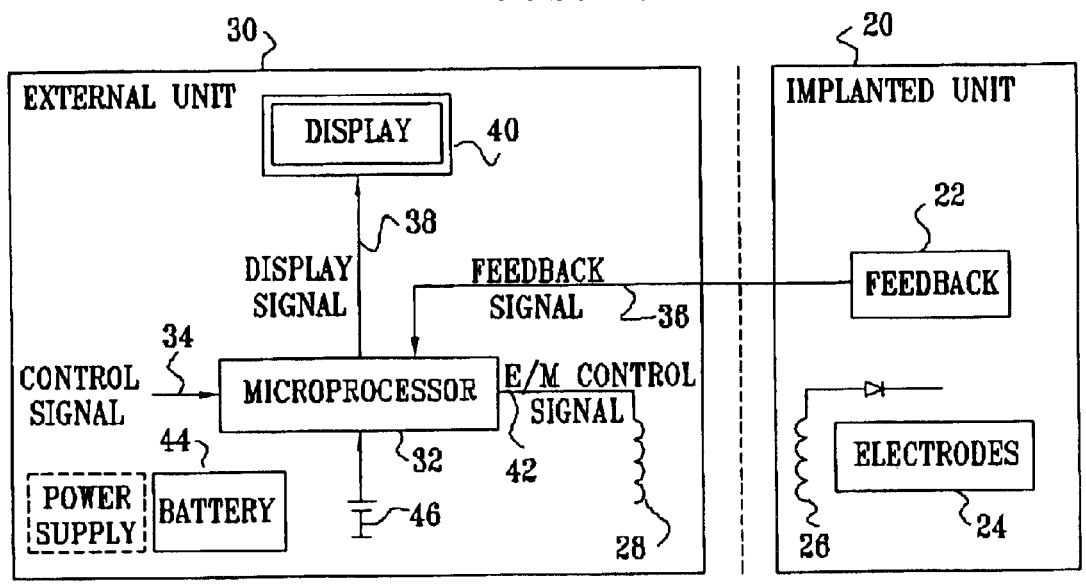
FIG. 3 is a schematic block diagram illustrating circuitry for use with the stimulator shown in FIG. 1, in accordance with a preferred embodiment of the present invention.

FIG. 3 is a schematic block diagram illustrating circuitry comprising an implanted unit 20 and an external unit 30, for use with stimulator 4 (FIG. 1), in accordance with a preferred embodiment of the present invention. Implanted unit 20 preferably comprises a feedback block 22 and one or more sensing or signal application electrodes 24. Implanted unit 20 typically also comprises an electromagnetic coupler 26, which receives power and/or sends or receives data signals to or from an electromagnetic coupler 28 in external unit 30.

External unit 30 preferably comprises a microprocessor 32 which receives an external control signal 34 (e.g., from a physician or from the patient), and a feedback signal 36 from feedback block 22. Control signal 34 may include, for example, operational parameters such as a schedule of operation, patient parameters such as the patient's weight, or signal parameters, such as desired frequencies or amplitudes of a signal to be applied to an MTS. If appropriate, control signal 34 can comprise an emergency override signal, entered by the patient or a healthcare provider to terminate stimulation or to modify it in accordance with a predetermined program. Microprocessor 32, in turn, preferably processes control signal 34 and feedback signal 36 so as to determine one or more parameters of the electric current to be applied through electrodes 24. Responsive to this determination, microprocessor 32 typically generates an electromagnetic control signal 42 that is conveyed by electromagnetic coupler 28 to electromagnetic coupler 26. Control signal 42 preferably corresponds to a desired current or voltage to be applied by electrodes 24 to an MTS, such as SPG 6, and, in a preferred embodiment, inductively drives the electrodes. The configuration of couplers 26 and 28 and/or other circuitry in units 20 or 30 may determine the intensity, frequency, shape, monophasic or biphasic mode, or DC offset of the signal (e.g., a series of pulses) applied to designated tissue.

Power for microprocessor 32 is typically supplied by a battery 44 or, optionally, another DC power supply. Grounding is provided by battery 44 or a separate ground 46. If appropriate, microprocessor 32 generates a display signal 38 that drives a display block 40 of external unit 30. Typically, but not necessarily, the display is activated to show feedback data generated by feedback block 22, or to provide a user interface for the external unit.

Implanted unit 20 is preferably packaged in a case made of titanium, platinum or an epoxy or other suitable biocompatible material. Should the case be made of metal, then the case may serve as a ground electrode and, therefore, stimulation typically is performed in a monopolar mode. Alternatively, should the case be made of biocompatible plastic material, two electrodes 24 are typically driven to apply current to the MTS.

For some applications, the waveform applied by one or more of electrodes 24 to designated tissue of an MTS (e.g., the SPG) comprises a waveform with an exponential decay, a ramp up or down, a square wave, a sinusoid, a saw tooth, a DC component, or any other shape known in the art to be suitable for application to tissue. Alternatively or additionally, the waveform comprises one or more bursts of short shaped or square pulses—each pulse preferably less than about 1 ms in duration. Generally, appropriate waveforms and parameters thereof are determined during an initial test period of external unit 30 and implanted unit 20. For some applications, the waveform is dynamically updated according to measured physiological parameters, measured during a period in which unit 20 is stimulating an MTS, and/or during a non-activation (i.e., standby) period.

In the case of migraine treatment, the waveform may take the form of a slowly varying shape, such as a slow saw tooth, or a constant DC level, intended to block outgoing parasympathetic messaging.

Figure 4:
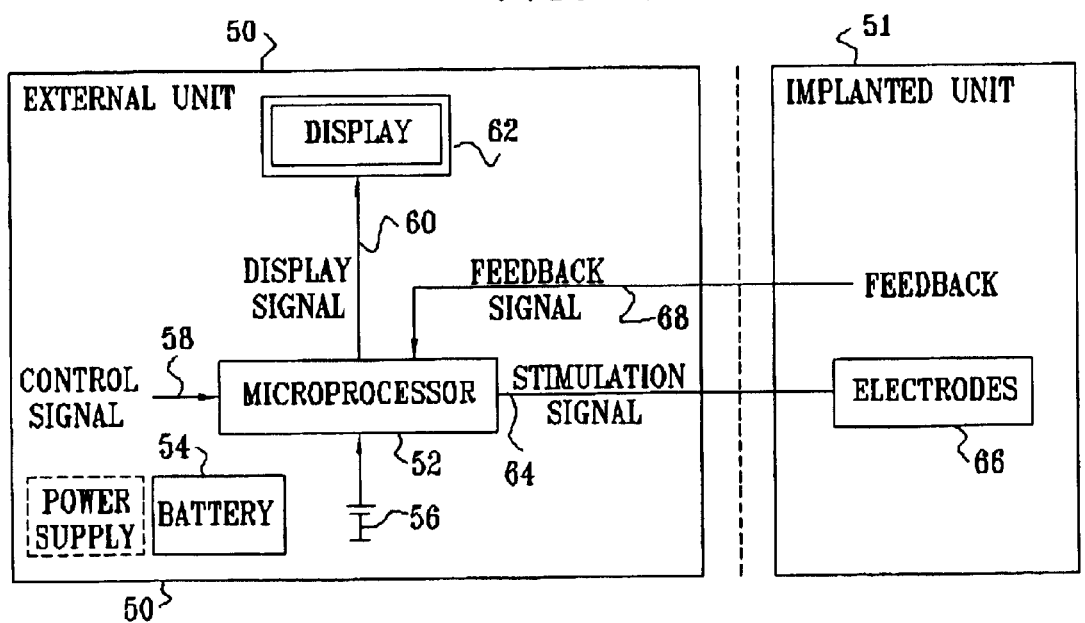
FIG. 4 is a schematic block diagram illustrating circuitry for use with the stimulator shown in FIG. 2, in accordance with a preferred embodiment of the present invention.

FIG. 4 is a schematic block diagram of circuitry for use, for example, in conjunction with control unit 8 (FIG. 2), in accordance with a preferred embodiment of the present invention. An external unit 50 comprises a microprocessor 52 supplied by a battery 54 or another DC power source. Grounding may be provided by battery 54 or by a separate ground 56. Microprocessor 52 preferably receives control and feedback signals 58 and 68 (analogous to signal 34 and 36 described hereinabove), and generates responsive thereto a stimulation signal 64 conveyed by one or more electrodes 66 to an MTS or other tissue. Typically, but not necessarily, feedback signal 68 comprises electrical feedback measured by one or more of electrodes 66 and/or feedback from other sensors on or in the patient's brain or elsewhere coupled to the patient's body. If appropriate, microprocessor 52 generates a display signal 60 which drives a display block 62 to output relevant data to the patient or the patient's physician. Typically, some or all of electrodes 66 are temporarily implanted in the patient (e.g., following a stroke), and are directly driven by wires connecting the external unit to the implanted unit.

Figure 5A:
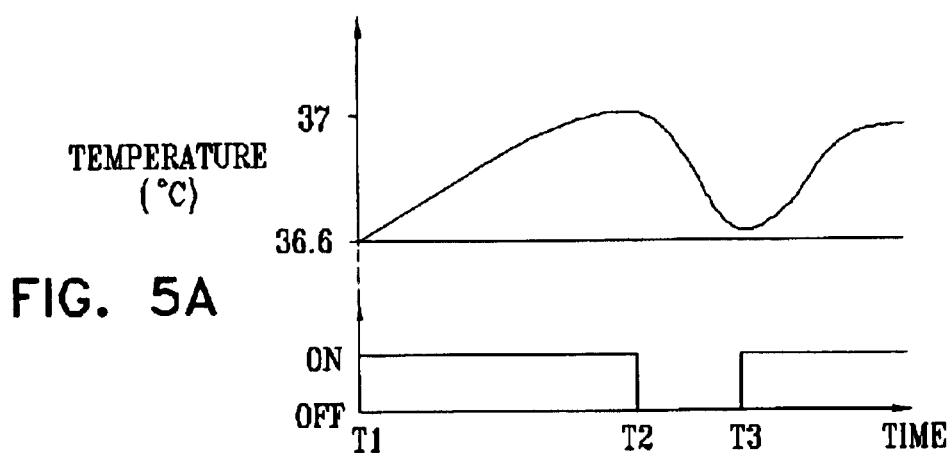
FIGS. 5A and 5B are schematic illustrations depicting different modes of operation of stimulators such as those shown in FIGS. 1 and 2, in accordance with preferred embodiments of the present invention.

FIG. 5A is a graph schematically illustrating a mode of operation of one or more of the devices shown in FIGS. 1–4, in accordance with a preferred embodiment of the present invention. Preferably, the effect of the applied stimulation is monitored by means of a temperature transducer at an MTS (e.g., the SPG) or elsewhere in the head, e.g., in the nasal cavity. As shown in FIG. 5A for a step (ON/OFF) mode of stimulation, stimulation of an MTS or related tissue is initiated at a time T1, and this is reflected by a measurable rise in temperature (due to increased blood flow). Once the temperature rises to a predetermined or dynamically-varying threshold (e.g., 37° C.), stimulation is terminated (time T2), responsive to which the temperature falls. As appropriate, when the temperature drops to a designated or dynamically-determined point, the stimulation is reinitiated (time T3). Preferably, suitable temperatures or other physiological parameters are determined for each patient so as to provide the optimal treatment. If appropriate, control instructions may also be received from the patient, e.g., to initiate stimulation upon the onset of a migraine headache.

Figure 5B:
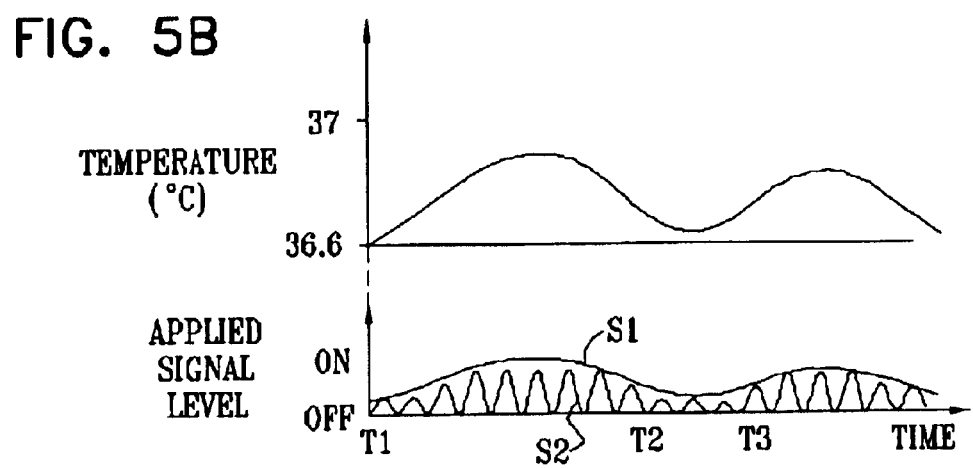

FIG. 5B is a graph schematically illustrating a mode of operation of one or more of the devices shown in FIGS. 1–4, in accordance with another preferred embodiment of the present invention. In this embodiment, the amplitude of the waveform applied to an MTS is varied among a continuous set of values (S1), or a discrete set of values (S2), responsive to the measured temperature, in order to achieve the desired performance. It will be appreciated that other feedback parameters measured in the head (e.g., intraocular pressure, intracranial pressure and/or cerebral blood flow), as well as measured systemic parameters (e.g., heart rate) and subjective patient inputs (e.g., migraine pain=3/5) may be used in conjunction with or separately from temperature measurements, in order to achieve generally optimal performance of the implanted apparatus.

Figure 6:
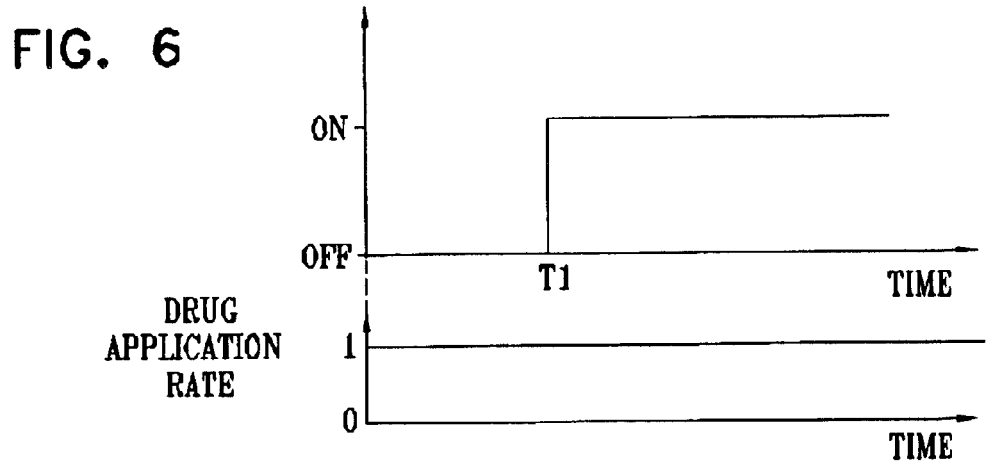
FIG. 6 is a schematic illustration of a mode of operation of the stimulators shown in FIGS. 1 and 2, synchronized with a drug delivery system, in accordance with a preferred embodiment of the present invention.

FIG. 6 is a graph schematically illustrating a mode of operation of one or more of the devices shown in FIGS. 1–4, in accordance with a preferred embodiment of the present invention. In this embodiment, a drug is administered to the patient at a constant rate, e.g., intravenously, prior to the initiation of chemical, mechanical, electrical and/or odorant stimulation of an MTS at time T1. Advantageously, this prior generation of heightened concentrations of the drug in the blood tends to provide relatively rapid transfer of the drug across the BBB and into the brain, without unnecessarily prolonging the enhanced permeability of the BBB while waiting for the blood concentration of the drug to reach an appropriate level. Alternatively, for some applications it is desirable to give a single injection of a bolus of the drug shortly before or after initiation of stimulation of an MTS. Typically, combined administration and stimulation schedules are determined by the patient's physician based on the biochemical properties of each drug targeted at the brain.

Figure 7:
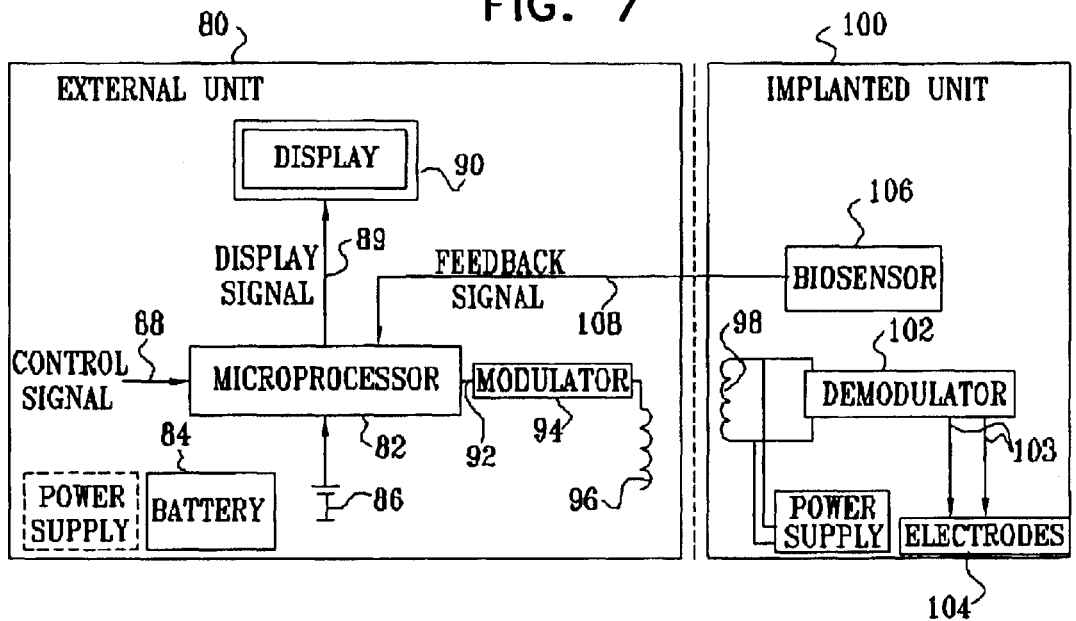
FIG. 7 is a schematic block diagram illustrating circuitry for use with the stimulator shown in FIG. 1, where the stimulator is driven by an external controller and energy source using a modulator and a demodulator, in accordance with a preferred embodiment of the present invention.

FIG. 7 is a schematic block diagram showing circuitry for parasympathetic stimulation, which is particularly useful in combination with the embodiment shown in FIG. 1, in accordance with a preferred embodiment of the present invention. An external unit 80 preferably comprises a microprocessor 82 that is powered by a battery 84 and/or an AC power source. Microprocessor 82 is grounded through battery 84 or through an optional ground 86.

In a typical mode of operation, an external control signal 88 is input to microprocessor 82, along with a feedback signal 108 from one or more biosensors 106, which are typically disposed in a vicinity of an implanted unit 100 or elsewhere on or in the patient's body. Responsive to signals 88 and 108, microprocessor 82 preferably generates a display signal 89 which drives a display 90, as described hereinabove. In addition, microprocessor 82 preferably processes external control signal 88 and feedback signal 108, to determine parameters of an output signal 92, which is modulated by a modulator 94. The output therefrom preferably drives a current through an electromagnetic coupler 96, which inductively drives an electromagnetic coupler 98 of implanted unit 100. A demodulator 102, coupled to electromagnetic coupler 98, in turn, generates a signal 103 which drives at least one electrode 104 to apply current to an MTS or to other tissue, as appropriate.

Preferably, biosensor 106 comprises implantable or external medical apparatus including, for example, one or more of the following:

- a blood flow sensor,
- a temperature sensor,
- a chemical sensor,
- an ultrasound sensor,
- transcranial Doppler (TCD) apparatus,
- laser-Doppler apparatus,
- a systemic or intracranial blood pressure sensor (e.g., comprising a piezoelectric crystal or capacitive sensor fixed to a major cerebral blood vessel, capable of detecting a sudden blood pressure increase indicative of a clot),
- an intraocular pressure sensor, e.g., comprising a piezoelectric crystal or capacitive sensor coupled to the nasal (medial) wall of the orbit, or at another site suitable for measuring intraocular pressure,
- a tissue vitality sensor, e.g., comprising laser Doppler or other optical apparatus for detecting a NAD/NADH ratio in tissue,
- a kinetics sensor, comprising, for example, an acceleration, velocity, or level sensor (e.g., a mercury switch), for indicating body dispositions such as a sudden change in body attitude (as in collapsing),
- an electroencephalographic (EEG) sensor comprising EEG electrodes attached to, or implanted in, the patients head, for indicating changes in neurological patterns, such as symptoms of stroke or migraine,
- a blood vessel clot detector (e.g., as described hereinbelow with reference to FIG. 13), or
- other monitors of physiological quantities suitable for carrying out the objects of this or other embodiments of the present invention.

Figure 8:
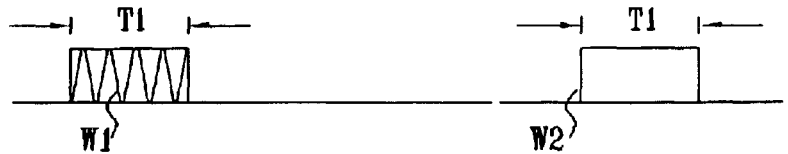
FIG. 8 depicts sample modulator and demodulator functions for use with the circuitry of FIG. 7, in accordance with a preferred embodiment of the present invention.

FIG. 8 is a schematic illustration showing operational modes of modulator 94 and/or demodulator 102, in accordance with a preferred embodiment of the present invention. The amplitude and frequency of signal 92 in FIG. 7 can have certain values, as represented in the left graph; however, the amplitude and frequency are modulated so that signal 103 has different characteristics.

Figure 9:
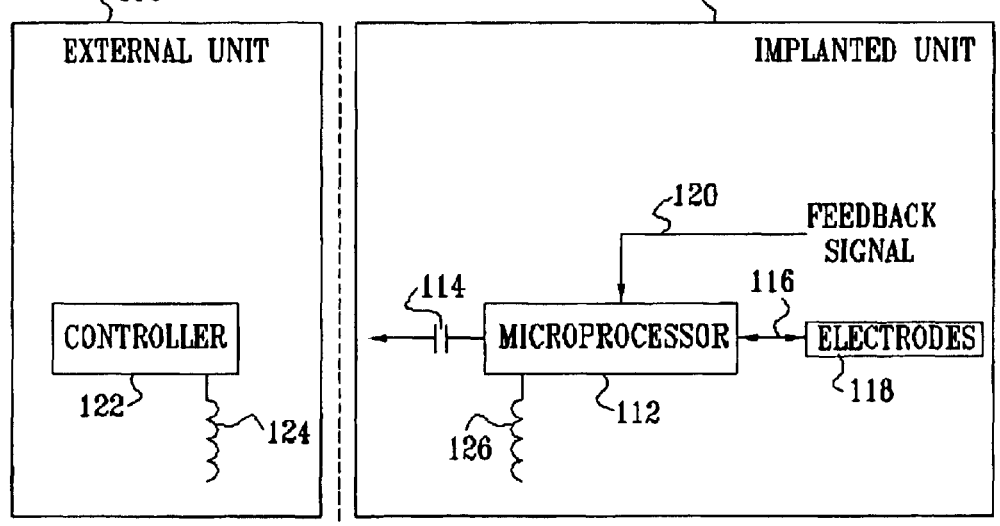
FIGS. 9, 10A, and 10B are schematic diagrams illustrating further circuitry for use with implantable stimulators, in accordance with respective preferred embodiments of the present invention.

FIG. 9 is a schematic illustration of further apparatus for stimulation of an MTS, in accordance with a preferred embodiment of the present invention. In this embodiment, substantially all of the processing and signal generation is performed by circuitry in an implanted unit 110 in the patient, and, preferably, communication with a controller 122 in an external unit 111 is performed only intermittently. The implanted unit 110 preferably comprises a microprocessor 112 coupled to a battery 114. Microprocessor 112 generates a signal 116 that travels along at least one electrode 118 to stimulate the MTS. A feedback signal 120 from a biosensor (not shown) and/or from electrode 118 is received by microprocessor 112, which is adapted to modify stimulation parameters responsive thereto. Preferably, microprocessor 112 and controller 122 are operative to communicate via wireless couplers 126 and 124 (e.g., electromagnetic couplers), in order to exchange data or to change parameters. Further preferably, battery 114 is wirelessly rechargeable (e.g., inductively rechargeable by electromagnetic coupling).

Figure 10A:
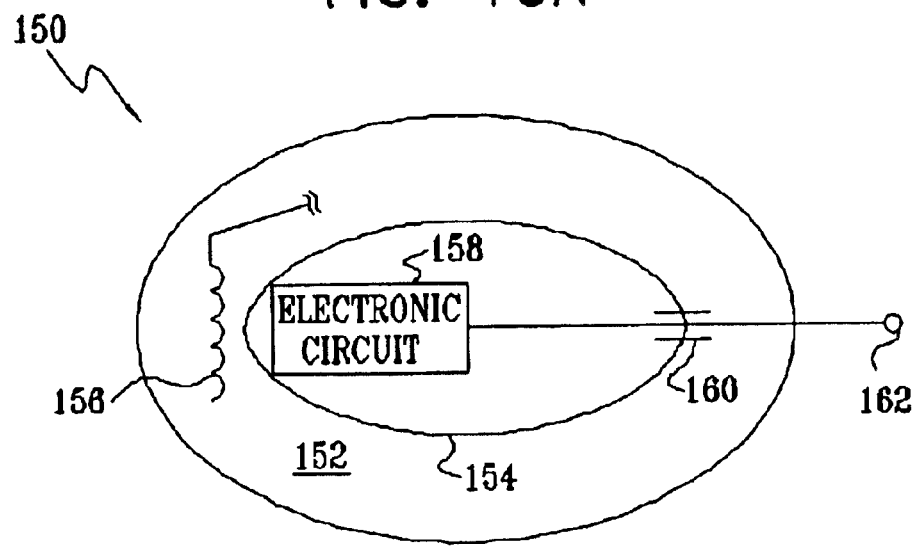

FIG. 10A is a schematic illustration of a stimulator 150, in accordance with a preferred embodiment of the present invention. Preferably, substantially all of the electronic components (including an electronic circuit 158 having a rechargeable energy source) are encapsulated in a biocompatible metal case 154. An inductive coil 156 and at least one electrode 162 are preferably coupled to circuit 158 by means of a feed-through coupling 160. The inductive coil is preferably isolated by an epoxy coating 152, which allows for higher efficiency of the electromagnetic coupling.

Figure 10B:
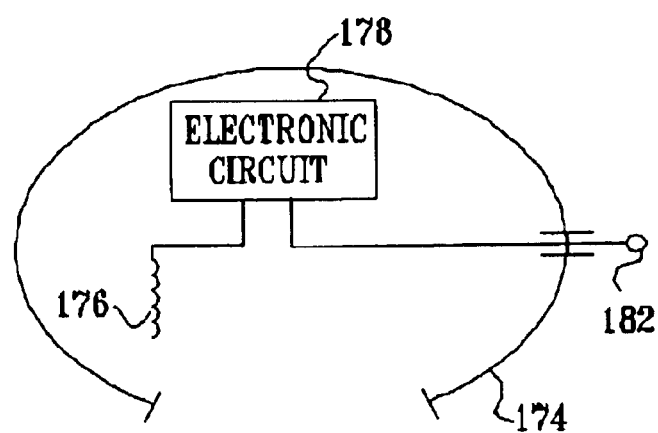

FIG. 10B is a schematic illustration of another configuration of an implantable stimulator, in accordance with a preferred embodiment of the present invention. Preferably, substantially all of the electronic components (including an inductive coil 176 and an electronic circuit 178 having a rechargeable energy source) are encapsulated in a biocompatible metal case 174. One or more feed-throughs are preferably provided to enable coupling between at least one electrode 182 and the electronic circuit, as well as between inductive coil 176 and another inductive coil (not shown) in communication therewith.

With reference to FIGS. 10A and 10B, the energy source for electronic circuits 158 and 178 may comprise, for example, a primary battery, a rechargeable battery, or a super capacitor. For applications in which a rechargeable battery or a super capacitor is used, any kind of energizing means may be used to charge the energy source, such as (but not limited to) standard means for inductive charging or a miniature electromechanical energy converter that converts the kinetics of the patient movement into electrical charge. Alternatively, an external light source (e.g., a simple LED, a laser diode, or any other light source) may be directed at a photovoltaic cell in the electronic circuit. Further alternatively, ultrasound energy is directed onto the implanted unit, and transduced to drive battery charging means.

Figure 11:
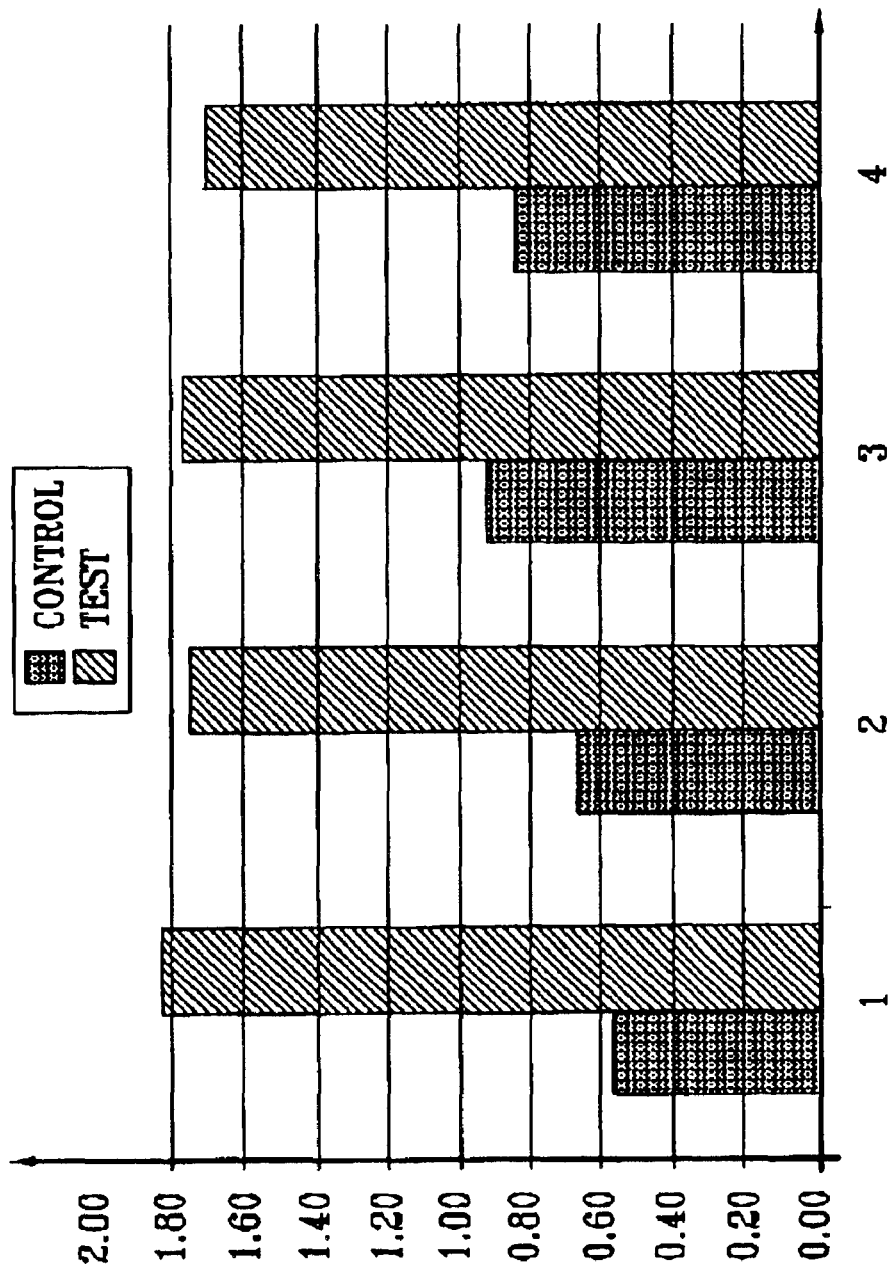
FIGS. 11 and 12 are bar graphs showing experimental data collected in accordance with a preferred embodiment of the present invention.
Figure 12:
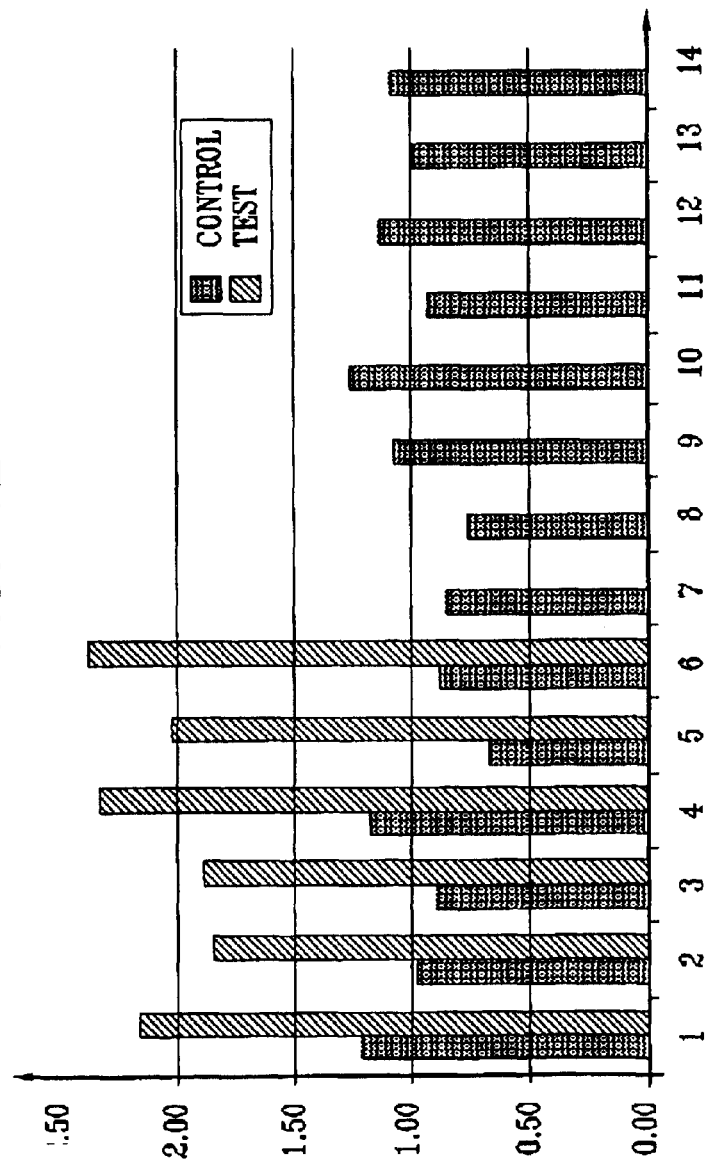

FIGS. 11 and 12 are bar graphs showing experimental results obtained during rat experiments performed in accordance with a preferred embodiment of the present invention. A common technique in monitoring bio-distribution of materials in a system includes monitoring the presence and level of radio-labeled tracers. These tracers are unstable isotopes of common elements (e.g., Tc, In, Cr, Ga, and Gd), conjugated to target materials. The chemical properties of the tracer are used as a predictor for the behavior of other materials with similar physiochemical properties, and are selected based on the particular biological mechanisms that are being evaluated. Typically, a patient or experimental animal is placed on a Gamma camera, or target tissue samples can be harvested and placed separately into a well counter. For the purpose of the present set of experiments which were performed, the well counter method was chosen due to its higher sensitivity and spatial resolution. A series of experiments using 99Tc-DTPA (DTPA molecule conjugated to a 99-Technetium isotope) were performed. The molecular weight of 99Tc-DTPA is 458 Da, its lipophilicity is negative, and its electric charge is +1. These parameters are quite similar with pharmacological agents used in standard chemotherapy, such as tamoxifen, etoposide and irinotecan.

FIGS. 11 and 12 show results obtained using 99Tc-DTPA penetration assays using ordinary brain sampling techniques (FIG. 11) and peeled brain techniques (FIG. 12). The x-axis of each graph represents different experimental runs, and the y-axis of each graph is defined as: [(hemisphere radioactivity)/(hemisphere weight)]/[(total injected radioactivity)/(total animal weight)]. The results obtained demonstrate an average 2.5-fold increase in the penetration of 99Tc-DTPA to the rat brain. It is noted that these results were obtained by unilateral stimulation of the SPG. The inventors believe that bilateral SPG stimulation will approximately double drug penetration, relative to unilateral SPG stimulation.

In both FIG. 11 and FIG. 12, some animals were designated as control animals, and other animals were designated as test animals. In each group, the left and right hemispheres were tested separately, and the height of each bar represents, for a given animal and a given hemisphere, the normalized level of radioactivity as defined above. Thus, FIG. 11 shows results from a total of four test hemispheres and four control hemispheres. FIG. 12 shows results from six test hemispheres and fourteen control hemispheres. The juxtaposition of control and test bars in the bar graphs is not meant to imply pairing of control and test hemispheres.

Figure 13:
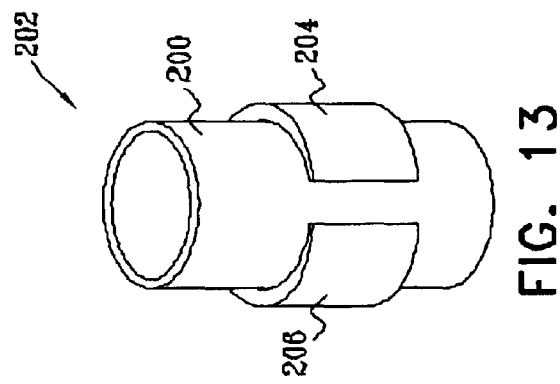
FIG. 13 is a schematic illustration of a sensor for application to a blood vessel, in accordance with a preferred embodiment of the present invention.

FIG. 13 is a schematic illustration of acoustic or optical clot detection apparatus 202, for use, for example, in providing feedback to any of the microprocessors or other circuitry described hereinabove, in accordance with a preferred embodiment of the present invention. The detection is preferably performed by coupling to a major blood vessel 200 (e.g., the internal carotid artery or aorta) a detecting element comprising an acoustic or optical transmitter/receiver 206, and an optional reflecting surface 204. Natural physiological liquids may serve as a mediating fluid between the device and the vessel. Preferably, the transmitter/receiver generates an ultrasound signal or electromagnetic signal which is reflected and returned, and a processor evaluates changes in the returned signal to detect indications of a newly-present clot. Alternatively, a transmitter is placed on side of the vessel and a receiver is placed on the other side of the vessel In either case, for some applications, more than one such apparatus 202 are placed on the vessel, in order to improve the probability of successful clot detection for possible estimation of the clot's direction of motion within the vessel, and to lower the false alarm (i.e. false detection) rate.

In a preferred embodiment of the present invention, an odorant is presented to an air passage of a patient, such as a nasal cavity or the throat, so as to increase BBB permeability so as to enhance delivery of an NSAID.

Figure 14:
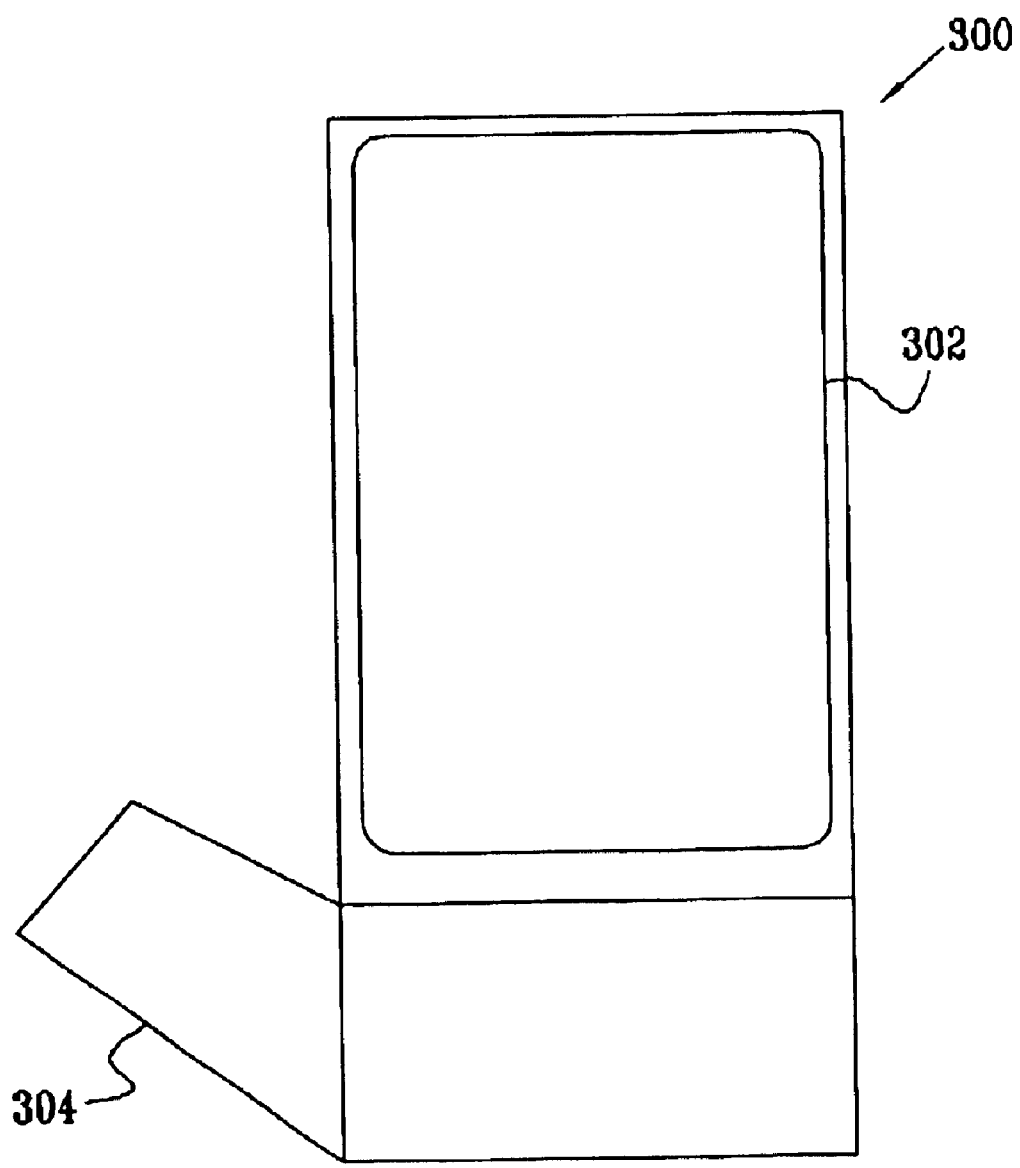
FIG. 14 is a schematic sectional illustration of a nasal inhaler, for use in presenting an odorant to a subject, in accordance with a preferred embodiment of the present invention.

FIG. 14 is a schematic sectional illustration of a nasal inhaler 300, for use in presenting an odorant to a subject, in accordance with a preferred embodiment of the present invention. Nasal inhaler 300 preferably comprises an apparatus known in the art, such as an aqueous spray nasal inhaler, a metered dose nasal inhaler, or an air-dilution olfactometer. The odorant is stored in an odorant-storage vessel 302, and is delivered to a nasal passage using an odorant-delivery element 304, such as a nasal piece. Alternatively or additionally, the odorant is presented by means of an orally-dissolvable capsule that releases the active odorants upon contact with salivary liquids. The odorants reach the appropriate neural structures and induce vasodilatation, vasoconstriction and/or cerebrovascular permeability changes. Delivery of an NSAID to the CNS or the eye can be achieved by mixing the NSAID with the odorant; by intravenously, intraperitoneally, or intramuscularly administering the NSAID while the odorant is having an effect, or therebefore; or by other delivery methods known in the art.

In a preferred embodiment of the present invention, stimulation of the MTS is achieved by applying a neuroexcitatory agent to the MTS. Suitable neuroexcitatory agents include, but are not limited to acetylcholine and urocholine. For some applications, the MTS is stimulated by applying a neuroinhibitory agent, such as atropine, hexamethonium, or a local anesthetic (e.g., lidocaine).

In a preferred embodiment of the present invention, stimulation of the MTS is achieved by applying mechanical stimulation to the MTS, e.g., vibration.

It is believed that substantially all pharmacological treatments aimed at cerebral cells (for example those used for treating neurological and psychiatric disorders and pathologies) are amenable for use in combination with techniques described herein, including electrical SPG system modulation and odorant presentation techniques. In particular, these embodiments of the present invention may be adapted for use in facilitating the administration of Non Steroidal Anti-Inflammatory Drugs (NSAIDS) to the CNS, including the brain and the spinal cord, or to the eye or ear.

These techniques facilitate the delivery of essentially all NSAIDs to the CNS, including, but not limited to, the following NSAIDs:

aspirin and other salicylates (e.g., magnesium salicylate)
Ibuprofen
naproxen
fenbufen
fenoprofen
flurbiprofen
ketoprofen
tiaprofenic acid
azapropazone
diclofenac
misoprostol
dexketoprofen
meloxicam
diflunisal
etodolac
indomethacin
mefenamic acid
nabumetone
phenylbutazone
piroxicam
sulindac
tenoxicam
aceclofenac
acematacin
choline subsalicylate
meclofenamate salsalate tolmetin selective NSAIDs, such as COX-2 inhibitors (e.g., celecoxib, rofecoxib)

Ketorolac

Oxaprozin

These techniques facilitate the delivery of NSAIDs to the CNS to treat (a) conditions of the CNS, including neurodegenerative and inflammatory conditions, and (b) peripheral conditions, including inflammatory conditions. Examples of conditions of the CNS that typically benefit from these techniques include inflammation of the brain; headaches, including migraines; neurodegenerative diseases; Alzheimer's disease; depression; lethargy; loss of appetite; multiple sclerosis; psychic disturbances (e.g., AIDS-related psychic disturbances); dementia (of known or unknown cause); and viral and bacterial infections. Examples of peripheral conditions that typically benefit from these techniques include muscle and joint pain, often caused by inflammation and/or infection. For some applications, these techniques are effective in treating peripheral conditions by means of mechanisms described in the above-cited article to Samad T A et al., or my means of other mechanisms.

In some embodiments of the present invention, techniques described herein are practiced in combination with techniques described in one or more of the above-cited co-assigned patent applications: (i) a U.S. provisional patent application to Lorian et al., filed on even date herewith, entitled, "Surgical tools and techniques for stimulation," (ii) a U.S. provisional patent application to Gross et al., filed on even date herewith, entitled, "Stimulation circuitry and control of electronic medical device," (iii) a U.S. patent application to Shalev et al., filed on even date herewith, entitled, "Stimulation for treating eye pathologies," and (iv) a U.S. provisional patent application to Shalev et al., filed on even date herewith, entitled, "Stimulation for treating ear pathologies." All of these applications are incorporated herein by reference. Alternatively or additionally, techniques described herein are practiced in combination with techniques described in one or more of the references cited in the Background section hereinabove.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description. For example, elements which are shown in a figure to be housed within one integral unit may, for some applications, be disposed in a plurality of distinct units. Similarly, apparatus for communication and power transmission which are shown to be coupled in a wireless fashion may be, alternatively, coupled in a wired fashion, and apparatus for communication and power transmission which are shown to be coupled in a wired fashion may be, alternatively, coupled in a wireless fashion.

What is claimed is:

1. A method for delivering a Non Steroidal Anti-Inflammatory Drug (NSAID) to at least a portion of a central nervous system (CNS) of a subject, comprising:

supplying the NSAID to a systemic blood circulation of the subject;

stimulating at least one site of the subject, the site selected from the list consisting of: a sphenopalatine ganglion (SPG) of the subject, an anterior ethmoidal nerve of the subject, a posterior ethmoidal nerve of the subject, a communicating branch between an anterior ethmoidal nerve and a retro-orbital branch of an SPG of the subject, a communicating branch between a posterior ethmoidal nerve and a retro-orbital branch of an SPG of the subject, a greater palatine nerve of the subject, a lesser palatine nerve of the subject, a sphenopalatine nerve of the subject, a communicating branch between a maxillary nerve and an SPG of the subject, a nasopalatine nerve of the subject, a posterior nasal nerve of the subject, an infraorbital nerve of the subject, an otic ganglion of the subject, an afferent fiber going into the otic ganglion of the subject, an efferent fiber going out of the otic ganglion of the subject, a vidian nerve of the subject, a greater superficial petrosal nerve of the subject, and a lesser deep petrosal nerve of the subject; and configuring the stimulation so as to cause an increase in passage of the NSAID from the systemic blood circulation across a blood brain barrier (BBB) of the subject to the portion of the CNS, during at least a portion of the time that the NSAID is present in the blood.

2. A method according to claim 1, wherein configuring the stimulation comprises configuring the stimulation so as to treat a condition of the CNS of the subject.

3. A method according to claim 2, wherein the condition of the CNS includes depression of the subject, and wherein configuring the stimulation comprises configuring the stimulation so as to treat the depression.

4. A method according to claim 2, wherein the condition of the CNS includes lethargy of the subject, and wherein configuring the stimulation comprises configuring the stimulation so as to treat the lethargy.

5. A method according to claim 2, wherein the condition of the CNS includes a loss of appetite of the subject, and wherein configuring the stimulation comprises configuring the stimulation so as to treat the loss of appetite.

6. A method according to claim 2, wherein the condition of the CNS includes multiple sclerosis of the subject, and wherein configuring the stimulation comprises configuring the stimulation so as to treat the multiple sclerosis.

7. A method according to claim 2, wherein the condition of the CNS includes a psychic disturbance of the subject, and wherein configuring the stimulation comprises configuring the stimulation so as to treat the psychic disturbance.

8. A method according to claim 2, wherein the condition of the CNS includes dementia of the subject, and wherein configuring the stimulation comprises configuring the stimulation so as to treat the dementia.

9. A method according to claim 2, wherein the condition of the CNS includes a neurodegenerative condition of the subject, and wherein configuring the stimulation comprises configuring the stimulation so as to treat the neurodegenerative condition.

10. A method according to claim 2, wherein the condition of the CNS includes an infection of the subject, and wherein configuring the stimulation comprises configuring the stimulation so as to treat the infection.

11. A method according to claim 2, wherein the condition of the CNS includes inflammation of a brain of the subject, and wherein configuring the stimulation comprises configuring the stimulation so as to treat the inflammation.

12. A method according to claim 1, wherein the condition of the CNS includes a headache of the subject, and wherein configuring the stimulation comprises configuring the stimulation so as to treat the headache.

13. A method according to claim 12, wherein the condition of the CNS includes a migraine headache of the subject, and wherein configuring the stimulation comprises configuring the stimulation so as to treat the migraine headache.

14. A method according to claim 12, wherein configuring the stimulation comprises configuring the stimulation so as to treat a peripheral condition of the subject.

15. A method according to claim 14, wherein the peripheral condition of the CNS includes pain in a joint of the subject, and wherein configuring the stimulation comprises configuring the stimulation so as to treat the joint pain.

16. A method according to claim 14, wherein the peripheral condition includes pain in a muscle of the subject, and wherein configuring the stimulation comprises configuring the stimulation so as to treat the muscle pain.

17. A method according to claim 14, wherein the peripheral condition includes pain caused by an infection of the subject, and wherein configuring the stimulation comprises configuring the stimulation so as to treat the pain.

18. A method according to claim 14, wherein the peripheral condition includes pain caused by an inflammation of the subject, and wherein configuring the stimulation comprises configuring the stimulation so as to treat the pain.

19. A method according to claim 1, wherein stimulating the site comprises stimulating the SPG of the subject, so as to cause the increase in passage of the NSAID.

20. A method according to claim 1, wherein stimulating the site comprises stimulating the anterior ethmoidal nerve of the subject, so as to cause the increase in passage of the NSAID.

21. A method according to claim 1, wherein stimulating the site comprises stimulating the posterior ethmoidal nerve of the subject, so as to cause the increase in passage of the NSAID.

22. A method according to claim 1, wherein stimulating the site comprises stimulating the communicating branch between the anterior ethmoidal nerve and the retro-orbital branch of the SPG of the subject, so as to cause the increase in passage of the NSAID.

23. A method according to claim 1, wherein stimulating the site comprises stimulating the communicating branch between the posterior ethmoidal nerve and the retro-orbital branch of the SPG of the subject, so as to cause the increase in passage of the NSAID.

24. A method according to claim 1, wherein stimulating the site comprises stimulating the greater palatine nerve of the subject, so as to cause the increase in passage of the NSAID.

25. A method according to claim 1, wherein stimulating the site comprises stimulating the lesser palatine nerve of the subject, so as to cause the increase in passage of the NSAID.

26. A method according to claim 1, wherein stimulating the site comprises stimulating the sphenopalatine nerve of the subject, so as to cause the increase in passage of the NSAID.

27. A method according to claim 1, wherein stimulating the site comprises stimulating the communicating branch between the maxillary nerve and the SPG of the subject, so as to cause the increase in passage of the NSAID.

28. A method according to claim 1, wherein stimulating the site comprises stimulating the nasopalatine nerve of the subject, so as to cause the increase in passage of the NSAID.

29. A method according to claim 1, wherein stimulating the site comprises stimulating the posterior nasal nerve of the subject, so as to cause the increase in passage of the NSAID.

30. A method according to claim 1, wherein stimulating the site comprises stimulating the infraorbital nerve of the subject, so as to cause the increase in passage of the NSAID.

31. A method according to claim 1, wherein stimulating the site comprises stimulating the otic ganglion of the subject, so as to cause the increase in passage of the NSAID.

32. A method according to claim 1, wherein stimulating the site comprises stimulating the afferent fiber going into the otic ganglion of the subject, so as to cause the increase in passage of the NSAID.

33. A method according to claim 1, wherein stimulating the site comprises stimulating the efferent fiber going out of the otic ganglion of the subject, so as to cause the increase in passage of the NSAID.

34. A method according to claim 1, wherein stimulating the site comprises stimulating the vidian nerve of the subject, so as to cause the increase in passage of the NSAID.

35. A method according to claim 34, wherein stimulating the site comprises stimulating the greater superficial petrosal nerve of the subject, so as to cause the increase in passage of the NSAID.

36. A method according to claim 34, wherein stimulating the site comprises stimulating the lesser deep petrosal nerve of the subject, so as to cause the increase in passage of the NSAID.

37. A method according to claim 1, wherein stimulating the site comprises driving a current into the site, and wherein configuring the stimulation comprises configuring the current so as to cause an increase in passage of the NSAID from the systemic blood circulation across the BBB to the portion of the CNS, during at least a portion of the time that the NSAID is present in the blood.

38. A method according to claim 1, wherein the site includes a first site and a second site, different from the first site, and wherein driving the current comprises driving the current between the first site and the second site.

39. A method according to claim 38,
wherein the first site includes the vidian nerve of the subject, and the second site includes the SPG of the subject, and
wherein driving the current comprises driving the current between the vidian nerve and the SPG.

40. A method according to claim 1, wherein stimulating the site comprises applying a chemical to the site, so as to stimulate the site.

41. A method according to claim 40, wherein applying the chemical comprises applying a neuroexcitatory agent to the site, so as to stimulate the site.

42. A method according to claim 41, wherein applying the neuroexcitatory agent comprises applying acetylcholine to the site, so as to stimulate the site.

43. A method according to claim 1, wherein stimulating the site comprises applying mechanical stimulation to the site, so as to stimulate the site.

44. A method according to claim 43, wherein applying the mechanical stimulation comprises applying vibration to the site, so as to stimulate the site.

* * * * *